United States Patent
Wistrand et al.

(10) Patent No.: US 10,577,459 B2
(45) Date of Patent: Mar. 3, 2020

(54) ALIPHATIC POLY(ESTER)S WITH THIOL PENDANT GROUPS

(71) Applicants: Anna Wistrand, Vällingby (SE); Daniela Pappalardo, Montoro (IT); Tiziana Fuoco, Oliveto Citra (IT)

(72) Inventors: Anna Wistrand, Vällingby (SE); Daniela Pappalardo, Montoro (IT); Tiziana Fuoco, Oliveto Citra (IT); Torbjörn Mathisen, Älvsjö (SE)

(73) Assignees: Anna Wistrand, Vällingby (SE); Daniela Pappalardo, Montoro (AV) (IT); Tiziana Fuoco, Oliveto Citra (SA) (IT)

( * ) Notice: Subject to any disclaimer, the term of this patent is extended or adjusted under 35 U.S.C. 154(b) by 0 days.

(21) Appl. No.: 15/768,347

(22) PCT Filed: Oct. 14, 2016

(86) PCT No.: PCT/EP2016/074785
§ 371 (c)(1),
(2) Date: Apr. 13, 2018

(87) PCT Pub. No.: WO2017/064291
PCT Pub. Date: Apr. 20, 2017

(65) Prior Publication Data
US 2018/0305495 A1    Oct. 25, 2018

Related U.S. Application Data

(60) Provisional application No. 62/242,064, filed on Oct. 15, 2015.

(51) Int. Cl.
| | |
|---|---|
| *C08G 63/688* | (2006.01) |
| *A01N 37/26* | (2006.01) |
| *A01N 37/36* | (2006.01) |
| *A61L 31/06* | (2006.01) |
| *A61L 31/14* | (2006.01) |
| *C07D 319/12* | (2006.01) |

(52) U.S. Cl.
CPC ......... *C08G 63/6882* (2013.01); *A01N 37/36* (2013.01); *A61L 31/06* (2013.01); *A61L 31/146* (2013.01); *C07D 319/12* (2013.01); *C08G 63/688* (2013.01); *A61L 2300/404* (2013.01)

(58) Field of Classification Search
CPC ......... A01N 37/26; A01N 37/36; A61L 31/06; A61L 31/14; C07D 319/12
See application file for complete search history.

(56) References Cited

U.S. PATENT DOCUMENTS
2012/0035341 A1    2/2012   Diehl et al.

FOREIGN PATENT DOCUMENTS
CN           103288788 A     9/2013

OTHER PUBLICATIONS

WO2010100390 machine translation, 2010.*
Dondoni, A., The Emergence of Thiol-Ene Coupling as a Click Process for Materials and Bioorganic Chemistry, Angew. Chem. Int. Ed., 47: 8995-8997, 2008.
Sinnwell, S. et al., Ring-Opening Homo- and Copolymerization of α-Methylene-ε-caprolactone, *Macromolecules*, 39: 2804-2807, 2006.
Gong, B. et al., New delta-valeroiactone derivatives useful for preparing flame retardant polyesters in the fields of drug delivery and protein protection, Database WPI, Week 201411, Thompson Scientific, London, GB, Abstract XP-002765119, Sep. 11, 2013.
Fuoco, T. et al., A Route to Aliphatic Poly(ester)s with Thiol Pendant Groups: From Monomer Design to Editable Porous Scaffolds, Biomacromolecules, 17: 1383-1394, 2016.
Kocienski, P., Chapter 5 Thiol Protecting Groups, in Protecting Groups, 3rd Edition, Georg Thieme Verlag, pp. 386-389, 2005.
Sisson, A. et al., Polyesters, Chapter 1 in Handbook of Biodegradable Polymers: Synthesis, Characterization and Applications, First Ed., Lendlein and Sisson (eds.), Wiley-VCH Verlag GmbH & co. KGaA, 2011.
English Translation of Chinese Patent CN103288788A.

* cited by examiner

*Primary Examiner* — Sun Jae Yoo
(74) *Attorney, Agent, or Firm* — Julie K. Staple; Dinsmore & Shohl LLP

(57) ABSTRACT

The present invention relates to a novel ester monomer susceptible to ring opening polymerization where the monomer comprise a functional group that may be transformed into thiols or S—S groups which allows further functionalization. The present invention also relates to polymers and co-polymers derived from said monomer.

18 Claims, No Drawings

ALIPHATIC POLY(ESTER)S WITH THIOL PENDANT GROUPS

FIELD OF THE INVENTION

The present invention describes a simple and controlled chemical synthetic approach that allow an efficient chemical pathway toward aliphatic polyesters with pendant editable side groups, the preparation of functionalized aliphatic poly (ester)s and co-polymers thereof.

BACKGROUND OF THE INVENTION

Given their versatile properties, synthetic polymeric materials have been employed in the biomedical field. Specifically, because of the biocompatibility and biodegradability, aliphatic poly(ester)s, such as poly(lactide) (PLA), poly(glycolide) (PGA), poly(ε-caprolactone) (PCL) and their copolymers, have become increasingly attractive in the design of temporary synthetic scaffolds in tissue engineering.

Their properties and degradation profiles can be precisely tuned to match the needs of the final application. Although their physical properties can be modulated via copolymerization, a major limitation to their application in highly specialized areas, such as the biomedical field, is the absence of readily accessible side-chain functionalities. The biofunctionalization of polyester-based scaffolds with biologically relevant ligands could provide a host of opportunities to control cell adhesion and functions. Specifically, conjugation with a peptide containing the sequence arginine-glycine-aspartic acid (Arg-Gly-Asp, or RGD) has been shown to improve the cytocompatibility and cellular attachment characteristics of temporary polymeric devices by promoting cellular adhesion through binding to integrin receptors. Therefore, the development of simple and controlled chemical synthetic approaches that allow the preparation of functionalized poly(ester)s is one of the main topics in this field.[1]

Two strategies can be followed to obtain polyesters with functionalities incorporated as side groups. First, post-polymerization modifications have been used to modify the surface of the polymers without impacting the bulk; however, these modifications are sometimes associated with side reactions, such as chain scission, with a consequent deterioration of the polymeric features.

The second method, co-polymerization with functionalized monomers, allows the preparation of editable polymers through the polymeric chain, which can affect the material in the bulk. Following the Kimura's pioneering approach, functionalized lactide- and glycolide-type monomers featuring pendant-protected carboxyl, hydroxyl and amino groups have been prepared by diazotization of available amino acids, such as aspartic and glutamic acids, serine or lysine, into the corresponding α-hydroxy acids, followed by cyclization.[2,3] Cyclic di-esters carrying aliphatic groups have also been obtained from their corresponding α-hydroxy acids. Attempts to obtain the analogous hydroxy acid starting from the diazotization reaction of the cysteine were unsuccessful.

Thiol synthesis, modification and functionalization are highly attractive and efficient in polymer and materials science and have immense application in biological therapeutics and drug delivery. The abundance of the thiol-based amino acid cysteine may allow the use of thiol chemistry to easily conjugate polymers with peptides or proteins.[4] Moreover, the thiol-ene click reaction represents an efficient tool for further polymer modifications. Following the example of nature, where disulfide bond formation plays an important role in the folding and stability of biopolymers, the oxidation of thiols into the corresponding disulphides should also be exploited as stimuli-responsive linkages to obtain improved and intelligent materials. Different approaches for the preparation of poly(ester)s with mercapto groups have already been reported. Exploiting their chemical structure, PCL samples functionalized with a thiol group on the chain-ends have been prepared.[5] Additionally, amphiphilic PLA-based block copolymers functionalized with disulfides at the block junctions have been described.[6] Alternatively, poly(ester)s with thiol pendant groups grafted throughout the polymeric chains have been obtained by polycondensation reaction approaches, enzyme-catalyzed chemoselective reactions of mercaptosuccinate with different diols,[7] or the polycondensation of dicarboxylic acid-containing thiol groups and diols in the presence of a metal initiator.[8] In this regard, we previously reported the polycondensation of suitably prepared sulfur-functionalized hydroxy acids, which afforded low molecular weight samples.[9]

In view of orthogonality conflicts and considering their instability toward oxidation and incompatibility with many polymerization processes, several strategies to protect thiols and thus prevent unwanted reactions have been developed and optimized.[10] We have also previously described a route to aliphatic poly(ester)s with thiol pendant groups.[11]

SUMMARY OF THE INVENTION

Due to the ubiquity of thiol groups in the biological environment and the versatility of thiol chemistry, the present inventors envisaged a lactide-type monomer featuring a protected thiol group as an attractive "building block" for the synthesis of functionalized aliphatic poly(ester)s. The polymerization of such a monomer could be a promising approach to combine the biodegradability of the aliphatic poly(ester) main chain with the great pliability of the pendant thiol groups.

With respect to the polycondensation reaction of hydroxy acids or dicarboxylic acid with diols, the ring-opening polymerization (ROP) of cyclic esters, mainly when promoted by metal-based catalysts in a coordination-insertion mechanism, can offer higher molecular weight, narrower dispersity, and better control in the microstructure of the final aliphatic poly(ester)s.

Thus, in seeking an efficient chemical pathway toward aliphatic polyesters with pendant editable side groups, the ROP of a lactide-type monomer bearing a thiol group appeared as a challenging solution. The present disclosure relates to the synthesis of monomers, oligomers and polymers with pendant thiol groups.

Therefore in a first aspect the present invention relates to a monomer as defined in claim 1.

In a second aspect the present invention relates to an oligomer or polymer, having a structure according to formula (2):

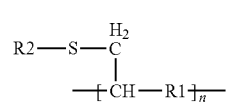

where n is an integer of 3 or higher
wherein $R_1$ is selected from a group consisting of

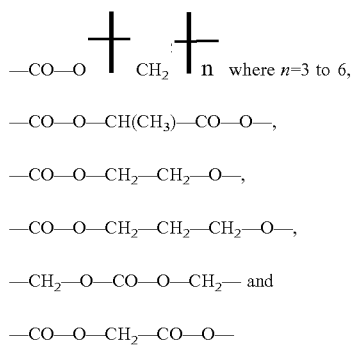 where $n=3$ to 6,

—CO—O—CH(CH$_3$)—CO—O—,

—CO—O—CH$_2$—CH$_2$—O—,

—CO—O—CH$_2$—CH$_2$—CH$_2$—O—,

—CH$_2$—O—CO—O—CH$_2$— and

—CO—O—CH$_2$—CO—O— and R$_2$ is any suitable leaving group that may be cleaved and give rise to the formation of a SH group or a S—S bond with proviso that said cleaving and formation does not degrade the ester bonds of the polyester chain.

In a third aspect the present invention relates to a copolymer containing from 1 to 95 mol % of a first monomer selected from the monomer according to any one of claims 1 to 4 and wherein the copolymer further contains at least one second monomer selected from a group consisting of the monomers glycolide, lactide (d,d- or 1,1-, meso or racemic mixture), trimethylene carbonate, caprolactone, paradioxanone, β-butyrolactone and 1,5-dioxepan-2-one.

In a fourth aspect the present invention relates to another polymer having a structure according to any one of formulas (3), (4) or (5):

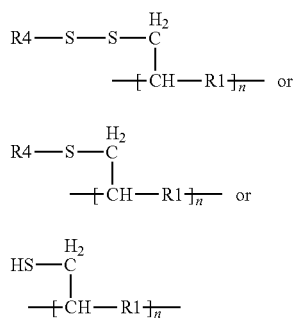

wherein n is an integer of 3 or higher,
wherein R$_1$ is selected from a group consisting of

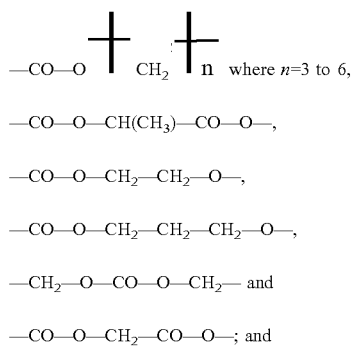 where $n=3$ to 6,

—CO—O—CH(CH$_3$)—CO—O—,

—CO—O—CH$_2$—CH$_2$—O—,

—CO—O—CH$_2$—CH$_2$—CH$_2$—O—,

—CH$_2$—O—CO—O—CH$_2$— and

—CO—O—CH$_2$—CO—O—; and

R4 is selected from an alkyl, phenyl, benzyl, pyridyl group, alkyl amide, alkyl ester or a polymer such as a polyester or polyether, or a peptide sequence containing a cysteine unit.

In a fifth aspect the present invention relates to another co-polymer containing from 1 to 95 mol % of a first monomer having a structure according to any one of formulas (6), (7) or (8):

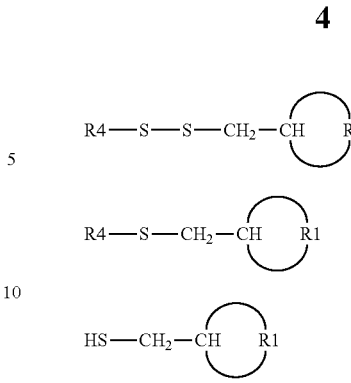

or where the first monomer has the repeating unit structure according to formula (3), (4) or (5) where n is an integer of 1 or higher; and
wherein the copolymer further contains at least one second monomer selected from the monomers glycolide, lactide (d,d- or 1,1-, meso or racemic mixture), trimethylene carbonate, caprolactone, paradioxanone, β-butyrolactone or 1,5-dioxepan-2-one;
wherein R$_1$ is selected from a group consisting of

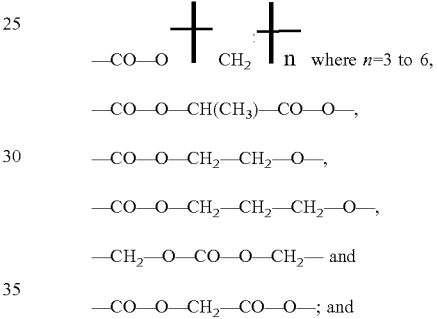 where $n=3$ to 6,

—CO—O—CH(CH$_3$)—CO—O—,

—CO—O—CH$_2$—CH$_2$—O—,

—CO—O—CH$_2$—CH$_2$—CH$_2$—O—,

—CH$_2$—O—CO—O—CH$_2$— and

—CO—O—CH$_2$—CO—O—; and

R4 is selected from an alkyl, phenyl, benzyl, pyridyl group, alkyl amide, alkyl ester or a polymer such as a polyester or polyether, or a peptide sequence containing a cysteine unit.

In a sixth aspect the present invention relates to the use of the polymer according to the present invention for reducing microbial contamination or biofilm formation.

In a seventh aspect the present invention relates to a medical device comprising the polymer according to the present invention.

In an eighth aspect the present invention relates to an implant comprising the polymer according to the present invention.

In a ninth aspect the present invention relates to a film comprising the polymer according to the present invention.

In a tenth aspect the present invention relates to nanoparticles comprising the polymer according to the present invention.

In an eleventh aspect the present invention relates to a polymer composition comprising a first polymer wherein the first polymer is a co-polymer according to the present invention and a second polymer comprising at least one monomer selected from the group consisting of glycolide, lactide (d,d- or 1,1-, meso or racemic mixture), trimethylene carbonate, caprolactone, paradioxanone, β-butyrolactone and 1,5-dioxepan-2-one.

DETAILED DESCRIPTION OF THE INVENTION

The present invention relates to a new type of monomers having S—S pendant group or a protected S—S or thiol group that may be converted into a S—S group or a thiol group. The present invention further relates to polymers derived from the new monomers and polymers derived from the new monomers where the protected groups have been converted.

In the present application molecular weights ($M_n$ and $M_w$) and molecular weight dispersities ($M_w/M_n$) were measured by size exclusion chromatography (SEC). The measurements were performed at 30° C. on a Verotech PL-GPC 50 Plus system equipped with two PLgel 5 μm MIXED-D (300×7.5 mm) columns, a PL-RI detector (Varian, Germany) and a PL-GPC 50 Plus autosampler using $CHCl_3$ as the eluent (1.0 mL $min^{-1}$). Narrow polystyrene standards were used as reference, and the flow rate fluctuations were corrected using toluene as an internal standard.

The Monomer

The present invention solves the problem of providing polyesters with pendant groups or pendant chains along the polyester back bone by providing a monomer having a protected thiol or S—S group. These protected groups may, after polymerization, be converted into thiol or S—S groups susceptible to further functionalization.

The monomer according to the present invention is an ester monomer that is susceptible to ROP using well known technique. The monomer has the structure according to formula (1)

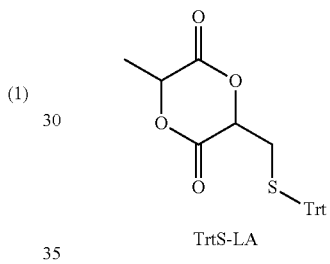

wherein $R_1$ is selected from a group consisting of

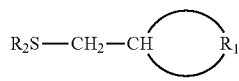 where $n$=3 to 6,

—CO—O—CH(CH$_3$)—CO—O—,

—CO—O—CH$_2$—CH$_2$—O—,

—CO—O—CH$_2$—CH$_2$—CH$_2$—O—,

—CH$_2$—O—CO—O—CH$_2$— and

—CO—O—CH$_2$—CO—O— and $R_2$ is any suitable leaving group. R2 is a leaving group that when cleaved will result in a SH group or a S—S bond. This cleaving reaction may be done using any suitable technique and reactants but the cleaving and the formation of the S—S or thiol group should not affect, at least not to any major extent, the other bonds in the polymer. For example, the reaction should not degrade the polyester chain for example by hydrolyzing the ester bonds to any major extent since it would then degrade the formed polyester. This cleaving and formation is preferably performed after polymerization of the monomer. R2 may also be a group containing an S—S bond or a SH group.

The R2 may be selected from a group consisting of p-methylbenzyl, p-methoxybenzyl, trityl, monomethoxytrityl, trimethoxybenzyl, 9-xanthenyl, 2,2,4,6,7-pentamethyl-5-dihydrobenzofuranylmethyl, benzyl, tert-butyl, 1-adamantyl, 2-(2,4-dinitrophenyl)ethyl, acetamidomethyl, phenylacetamidomethyl, tert-butylmercapto, 3-nitro-2pyridinesulfenyl, 2-pyridinesulfenyl, allyloxycarbonyl, phenylacetamidomethyl, 5-tert-butylmercapto, 3-nitro-2-pyridinesulfenyl, 2-pyridinesulfenyl, allyloxycarbonyl, N-allyloxycarbonyl-N-[2,3,5,6-tetrafluoro-4-8phenylthio) phenyl]aminomethyl, o-nitrobenzyl and 4-picolyl. In one embodiment R2 is selected from the group consisting of p-methylbenzyl; p-methoxybenzyl; trityl, monomethoxytrityl; trimethoxybenzyl; 9-xanthenyl; 2,2,4,6,7-pentamethyl-5-dihydrobenzofuranylmethyl, benzyl, tert-butyl; 1-adamantyl; 2-(2,4-dinitrophenyl)ethyl; acetamidomethyl; phenylacetamidomethyl; tert-butylmercapto; 3-nitro-2pyridinesulfenyl; 2-pyridinesulfenyl; allyloxycarbonyl; 4-picolyl. In another embodiment R2 is a trityl group.

The monomer is preferably derived from glycolide, lactide (d,d- or l,l-, meso or racemic mixture), trimethylene carbonate, caprolactone, paradioxanone, β-butyrolactone or 1,5-dioxepan-2-one. In one embodiment the monomer is derived from lactide i.e. R1 is CO—O—CH(CH$_3$)—CO—O—. In one embodiment the monomer is 3-methyl-6-(tritylthiomethyl)-1,4-dioxane-2,5-dione where R1 is CO—O—CH(CH$_3$)—CO—O— and R2 is a trityl group as disclosed in Chart 1.

Chart 1. The monomer 3-methyl-6-(tritylthiomethyl)-1,4-dioxane-2,5-dione (TrtS-LA).

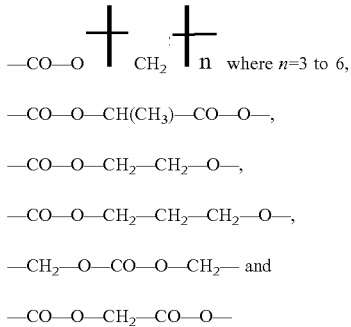

TrtS-LA

In a schematic description of the monomer synthesis, the synthesis is performed in two or more steps where the first step is a halogenation of the cyclic ester preferably glycolide, lactide (d,d- or l,l-, meso or racemic mixture), trimethylene carbonate, caprolactone, paradioxanone, β-butyrolactone or 1,5-dioxepan-2-one. This may be done by radical bromination, for example with N-bromosuccinimide. In the second step a dehydrohalogenation is done for example by using a suitable base such as trimethylamine. In the subsequent step the cyclic ester is functionalized to comprise the final —CH2-SR2 using any suitable technique and chemistry known to a skilled person. This may be done for example by reacting the product from the second step with a suitable thiol, for example triphenylmethanethiol and a base such as triethylene amine. The monomer synthesis may be performed in an inert atmosphere such as nitrogen and it may be done in a suitable solvent such as acetonitrile. The reactions may be performed at room temperature or at a temperature of 25-40° C. The final monomer may be isolated for example by liquid-liquid extraction or chromatography or a combination thereof. Example 1 provides a more detailed description of a non-limiting example of the synthesis.

Intermediate Polymer or Polymer with Protected S—S or SH Groups

Polymerizing the monomer according to the present invention may be done using standard and well known ROP techniques and conditions. The monomer or monomers may be dried prior to polymerization. For example the polymerization may be initiated using a nucleophile such as an alcohol or a diol and the polymerization may be done together with a catalyst such as stannous octoate, diamine bisphenolate salan yttrium isopropoxide compound or salycilaldiminato aluminum complex. A copolymer may be prepared by adding another suitable monomer such as a cyclic ester or a by adding a premade oligomer or polymer of another suitable monomer such as a cyclic ester. A suitable solvent such as toluene may be used in the polymerization and the reaction temperature may be 40-110° C., preferably 60-80. The final polymer may be isolated by precipitation.

The polymer, or oligomer, is a polymer having a polyester backbone and pendant S—S groups or protected S—S or thiol groups. The polymer, or oligomer, obtained has the structure according to formula (2)

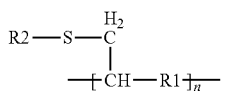

where n is an integer of 3 or higher. In one embodiment n is 10 or higher, or 20 or higher, or 30 or higher, or 40 or higher, or 50 or higher.

R1 and R2 are as defined previously. R1 is preferably CO—O—CH(CH$_3$)—CO—O— and R2 is preferably a trityl group.

The present invention further relates to a copolymer containing from 1 to 95 mol % of a first monomer selected from the monomer according to formula (1). The content may be 20 mol % or higher, or 40 mol % or higher, or 80 mol % or lower, or 60 mol % or lower. The copolymer further contains at least one second monomer selected from the group consisting of glycolide, lactide (d,d- or 1,1-, meso or racemic mixture), trimethylene carbonate, caprolactone, paradioxanone, β-butyrolactone and 1,5-dioxepan-2-one. In one embodiment the second monomer is lactide. In another embodiment the second monomer is caprolactone. In yet another embodiment the second monomer is trimethylene carbonate. In one embodiment the copolymer comprises at least two second monomers and wherein said at least two second monomers are selected from lactide, trimethylene carbonate, glycolide and caprolactone such as lactide and trimethylene carbonate, or caprolactone and trimethylene carbonate, or caprolactone and lactide, or trimethylene carbonate and glycolide, or caprolactone and glycolide, or lactide and glycolide. The molar ratio between the at least two second monomers may be from 1:20 to 20:1 such as 1:10 to 10:1. The copolymer may be a segmented copolymer where each segment is a diblock or a multiblock (n is 3 or higher), or the copolymer is random copolymer. Depending on the second monomer the mechanical properties and degradation time of the co-polymer may be tailored.

The number average molecular weight (M$_n$) of the copolymer is preferably at least 5,000 g/mol such as at least 10,000 g/mol, or at least 20,000 g/mol, or at least 25,000 g/mol. The dispersity may be less than 1.5, or less than 1.4, or less than 1.3.

The Polymer

The intermediate may be deprotected and further functionalized or associated with groups in order to obtain wanted properties. These properties may be tailored in respect to hydrophilicity, biological response, miscibility and so on. The polymer has the structure according to formula (3), (4) or (5)

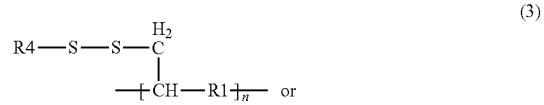

wherein n is an integer of 3 or higher. In one embodiment n is 10 or higher, or 20 or higher, or 30 or higher, or 40 or higher, or 50 or higher.

R1 is as defined in claim 1 and is preferably a CO—O—CH(CH$_3$)—CO—O—.

R4 is a group that has been connected to the polymer via the R2 group. R4 may be selected from an alkyl, phenyl, benzyl, pyridyl group, alkyl amide, alkyl ester or a polymer. The polymer may be a polyester or a polyether. The polymer may be a hydrophilic and/or an antibacterial polymer. In one embodiment the polymer is polyethylene glycol. The R4 may also be or comprise a peptide sequence containing a cysteine unit where the peptide sequence may be antibacterial. In one embodiment R4 is a peptide sequence comprising an RGD or and RGDC peptide sequence or a peptide sequence ending with C. In one embodiment the R4 is an alkyl amide such as ethyl heptanoylalaninate. In another embodiment the R4 is an alkyl ester such as ethyl-heptanoylate. The advantage of ethyl heptanoylalaninate and ethyl-heptanoylate is that they may be further functionalized for example by attaching amino acids via the ester groups. The number of R2 groups that have been converted into R4 groups may be 1-95 mol %, or at least 10 mol %, or at least 20 mol %.

In one embodiment the polymer has the structure according to formula (3) or (4).

As described above, by adding a suitable monomer other the monomer according to the present invention during polymerization a copolymer may be prepared. This copolymer may contain from 1 to 95 mol % of a first monomer having a structure according to formula (6), (7) or (8)

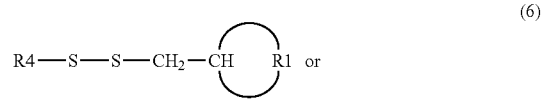

or where the first monomer has the repeating unit structure according to formula (3), (4) or (5) where n is an integer of 1 or higher. In one embodiment n is 2 or higher, or 3 or higher, or 5 or higher, or 10 or higher, or 20 or higher, or 30 or higher, or 40 or higher, or 50 or higher. In one embodiment the repeating unit structure is according to formula (3) or (4). The content of the first monomer may be 20 mol % or higher, or 40 mol % or higher, or 80 mol % or lower, or 60 mol % or lower.

The copolymer further contains at least one second monomer selected from the monomers glycolide, lactide (d,d- or 1,1-, meso or racemic mixture), trimethylene carbonate, caprolactone, paradioxanone, β-butyrolactone or 1,5-dioxepan-2-one.

R1 is as defined in claim 1 and is preferably CO—O—CH(CH$_3$)—CO—O—. R4 is selected from an alkyl, phenyl, benzyl, pyridyl group, alkyl amide such as ethyl heptanoylalaninate, or alkyl ester such as ethyl-heptanoylate a polymer. The polymer may be a polyester or a polyether. The polymer may be a hydrophilic and/or an antibacterial polymer. In one embodiment the polymer is polyethylene glycol. The R4 may also be or comprise a peptide sequence containing a cysteine unit where the peptide sequence may be antibacterial. In one embodiment R4 is a peptide sequence comprising an RGD or and RGDC peptide sequence or a peptide sequence ending with C.

In one embodiment the second monomer is lactide. In another embodiment the second monomer is caprolactone. In yet another embodiment the second monomer is trimethylene carbonate. In yet another embodiment the second monomer is glycolide. In one embodiment the copolymer comprises at least two second monomers and wherein said at least two second monomers are selected from glycolide, lactide, trimethylene carbonate and caprolactone such as glycolide and trimethylene carbonate, or lactide and trimethylene carbonate, or caprolactone and trimethylene carbonate, or caprolactone and lactide. The molar ratio between the at least two second monomers may be from 1:20 to 20:1 such as 1:10 to 10:1. The copolymer may be a segmented copolymer where each segment is a diblock or a multiblock (n is 3 or higher), or the copolymer may be a random copolymer.

The number average molecular weight ($M_n$) of the copolymer is preferably at least 1,000 g/mol such as at least 5,000 g/mol, or at least 10,000 g/mol, or at least 20,000 g/mol, or at least 25,000 g/mol. The dispersity may be less than 1.5, or less than 1.4, or less than 1.3.

Polymer Composition

The present invention further relates to polymer compositions comprising the polymer according to the present invention. The composition comprises, besides the polymer of the present invention, a second polymer. This second polymer is a degradable polymer, such as a degradable polyester or degradable polycarbonate, and may be polymers comprising a monomer selected from the group consisting of glycolide, lactide (d,d- or 1,1-, meso or racemic mixture), trimethylene carbonate, caprolactone, paradioxanone, β-butyrolactone and 1,5-dioxepan-2-one. In one embodiment the second polymer is poly(lactide), poly(caprolactone) or poly(trimethylene carbonate). In another embodiment the second polymer is a co-polymer comprising two or more of lactide, trimethylene carbonate or caprolactone monomers. The polymer composition may comprise 1-99 wt % of the first polymer (i.e. the polymer according to the present invention) and 1-99 wt % of the second polymer.

Applications

The present invention facilitates the preparation of polyesters with a variety of functional pending groups or chains. This makes the present invention very versatile and may be used in many different applications.

S—S or thiol groups along a degradable polymer main chain can be used to covalently attach different kinds of growth factors, entities that stimulate specific cell differentiation or attract a specific kind of proteins or cells. Designing 3D scaffolds from these polymers/copolymers can establish an in vitro 3D system for studying growth of cells in an authentic microenvironment. A polymer having pending thiol groups may be functionalized with a double bond according to thiol-ene chemistry, which opens up the field for further reactions.

The covalently attached groups, attached to the polyester via the S—S or thiol group, may reduce the microbial contamination or bio film formation. This can be of interest for medical implants or in vivo devices for example.

Films may be prepared from the polymer or co-polymer or the polymer composition according to the present invention. The preparation may be done by solvent casting or spinning. The films may also be prepared as a coating on a substrate such as a medical device. Nanoparticles may be prepared via S—S bond formation, including the polymers described in the present invention and other telechelic polymers ending with SH group, for example telechelic PEG bearing thiol groups at both ends, SH-PEG-SH. They may have application for drug delivery systems susceptible to glutathione redox environment. The nanoparticles can also be used as coating of medical devices. Nanoparticles may be prepared based on or comprising the polymer according to the present invention. In one embodiment gold nanoparticles comprise polymers according to the present invention where the polymers bind to the gold nanoparticles via their thiol groups.

EXAMPLES

General Description of the Synthesis

Moisture and air-sensitive materials were manipulated under nitrogen using Schlenk techniques or in an MBraun Labmaster glove box. Before use, glassware was dried overnight in an oven at 120° C. Solvents were refluxed over a drying agent (indicated below) and distilled under nitrogen: toluene and methanol (MeOH) over Na; xylenes, benzene and tetrahydrofuran (THF) over Na/benzophenone; and dichloromethane ($CH_2Cl_2$) over $LiAlH_4$. Acetonitrile ($CH_3CN$) was dried over $Na_2SO_4$ and stored over molecular sieves.

L-Lactide (LA) was purified by recrystallization from dry toluene and then dried in vacuo with phosphorous pentoxide ($P_2O_5$) for 96 hours. Benzoyl peroxide was purified by recrystallization from $CH_2Cl_2$ and MeOH and dried in a dessicator for two days. Trimethylamine ($NEt_3$) was dried over molecular sieves for two days. ε-Caprolactone (CL) was distilled in vacuo over $CaH_2$ and stored over molecular sieves in a drybox. Salicylaldiminato aluminum complex[12] and diamine bisphenolate salan yttrium isopropoxide compound were synthesized according to literature procedures. The H-Arg-Gly-Asp-Cys-OH peptide (RGDC) was purchased from Bachem and used as received. All other reagents and solvents were purchased from Sigma-Aldrich. Solvent and chemicals were used as received unless stated otherwise.

Molecular weights ($M_n$ and $M_w$) and molecular weight dispersities ($M_w/M_n$) were measured by size exclusion chromatography (SEC). The measurements were performed at 30° C. on a Verotech PL-GPC 50 Plus system equipped with two PLgel 5 μm MIXED-D (300×7.5 mm) columns, a PL-RI detector (Varian, Germany) and a PL-GPC 50 Plus autosampler using $CHCl_3$ as the eluent (1.0 mL min'). Narrow polystyrene standards were used as reference, and the flow rate fluctuations were corrected using toluene as an internal standard.

Example 1. Synthesis of 3-methyl-6-(tritylthiomethyl)-1,4-dioxane-2,5-dione (TrtS-LA)

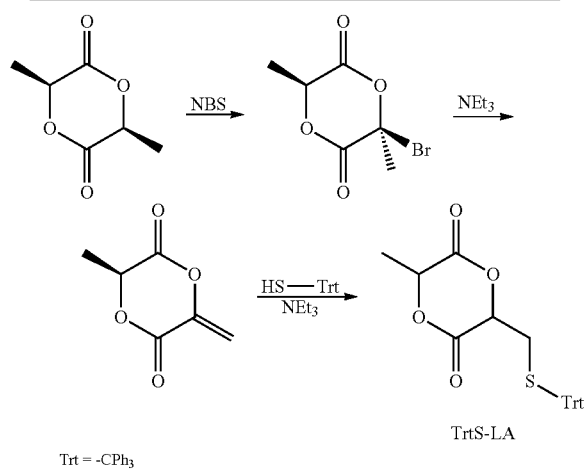

Scheme 1. Synthesis of 3-methyl-6-(tritylthiomethyl)-1,4-dioxane-2,5-dione (TrtS-LA) by modification of the L-lactide Trt = -CPh$_3$ The synthesis of (6S)-3-methylene-6-methyl-1,4-dioxane-2,5-dione was performed in two steps. L-lactide was converted into (3S,6S)-3-bromo-3,6-dimethyl-1,4-dioxane-2,5-dione by radical bromination with N-bromosuccinimide (NBS). Then, the dehydrobromination of the latter with trimethylamine (NEt$_3$) gave the (6S)-3-methylene-6-methyl-1,4-dioxane-2,5-dione. To a solution of triphenylmethanethiol (8.20 g; 29.6 mmol) and triethylamine (800 µL; 5.6 mmol) in dry CH$_3$CN (200 mL) was added dropwise a solution of (6S)-3-methylene-6-methyl-1,4-dioxane-2,5-dione (4.00 g; 28.2 mmol), dissolved in dry CH$_3$CN (80 mL), over 40 min at 0° C. under nitrogen. The reaction mixture was stirred for 1.5 hours at 0° C. The mixture was concentrated in vacuo to ~100 mL, dissolved in ethyl acetate (400 mL) and washed with HCl (200 mL×3; 0.1 M). The organic layer was dried over Na$_2$SO$_4$. Then, the solvent was evaporated to dryness. The resulting solid was purified by column chromatography (silica gel; eluent n-hexane/ethyl acetate in gradient).

Example 2. Copolymerization of 3-methyl-6-(tritylthiomethyl)-1,4-dioxane-2,5-dione (TrtS-LA) with L-Lactide (LA) in the Presence of Aluminum Complex Prior to polymerization, the TrtS-LA was dried as follow: the solid was dissolved in 100 mL of toluene, the solution was dried over Na$_2$SO$_4$. After filtration, the solvent was evaporated and the monomer was dissolved in dry toluene. The toluene was removed in vacuo trap by trap and the monomer was further dried with P$_2$O$_5$ for 96 hours and stored in glove box at −30° C. A 25 mL Schlenk Flask was charged sequentially with the salycilaldiminato aluminum complex, (10.0 mg; 25 µmop (or alternatively stannous octoate/alcohol functionalized molecule), LA (306 mg; 2.12 mmol) and Trt-LA (156 mg; 0.38 mmol) as monomers, toluene (2.0 mL), and MeOH (0.25 mL of a 0.1 M toluene solution; 25 µmop. The polymerization mixture was thermostated at 70° C. and magnetically stirred for 96 hours. Then, the mixture was cooled down to room temperature and poured in n-hexane. The precipitate was filtered, washed sequentially with n-hexane and MeOH and dried in vacuo at 30° C. overnight. $M_n$=21.2 kDa ($M_w/M_n$=1.1).

Example 3. Copolymerization of 3-methyl-6-(tritylthiomethyl)-1,4-dioxane-2,5-dione (TrtS-LA) with ε-Caprolactone (CL)

The polymerization was performed as above but TrtS-LA (314 mg; 0.75 mmol) and CL (200 mg; 1.75 mmol) were used as monomers. $M_n$=19.2 kDa ($M_w/M_n$=1.2).

Example 4. Copolymerization of 3-methyl-6-(tritylthiomethyl)-1,4-dioxane-2,5-dione (TrtS-LA) with ε-Caprolactone (CL) and L-Lactide (LA)

The polymerization was performed as above but TrtS-LA (105 mg; 0.25 mmol), CL (57.0 mg; 0.50 mmol) and LA (252 mg; 1.75 mmol) were used as monomers. $M_n$=25.9 kDa ($M_w/M_n$=1.4).

Example 5. Copolymerization of 3-methyl-6-(tritylthiomethyl)-1,4-dioxane-2,5-dione (TrtS-LA) with L-Lactide (LA) in the Presence of Stannous Octanoate A previously silanized 25 mL round-bottom flask was charged with stannous octanoate, SnOct$_2$ (5.0 mg; 12.0 nmol), ethylene glycol (3.0 mg; 50 µmol), LA (1.650 g; 11.4 mmol) and TrtS-LA (0.250 g; 0.60 mmol) as monomers. The polymerization mixture was thermostated at 110° C. and magnetically stirred for 24 hours. Then, the mixture was cooled down to room temperature, the crude copolymer was dissolved in CH$_2$Cl$_2$ and precipitated twice in cold MeOH. The precipitate was filtered, washed sequentially with MeOH and dried in vacuo at 30° C. overnight. Yield=76%. Composition TrtS-LA:LA=6:94. $M_n$=36.6 kDa ($M_w/M_n$=1.24).

Example 6. Copolymerization of 3-methyl-6-(tritylthiomethyl)-1,4-dioxane-2,5-dione (TrtS-LA) with L-Lactide (LA) and Glycolide (GA)

The polymerization was performed as above but TrtS-LA (0.250 g; 0.60 mmol), LA (0.960 g; 8.40 mmol) and GA (0.350 g; 0.30 mmol) were used as monomers. Yield=73%. Composition TrtS-LA:LA:GA=5.5:51:43.5. $M_n$=33.8 kDa ($M_w/M_n$=1.29).

Example 7. Copolymerization of 3-methyl-6-(tritylthiomethyl)-1,4-dioxane-2,5-dione (TrtS-LA) with L-Lactide (LA) and ε-Caprolactone (CL)

The polymerization was performed as above but TrtS-LA (0.200 g; 0.50 mmol), LA (0.900 g; 6.25 mmol) and CL (0.600 g; 0.52 mmol) were used as monomers. The polymerization mixture was magnetically stirred for 96 hours. Yield=50%.

Composition TrtS-LA:LA:CL=8:68:24. $M_n$=58.3 kDa ($M_w/M_n$=1.40).

Example 8. Copolymerization of 3-methyl-6-(tritylthiomethyl)-1,4-dioxane-2,5-dione (TrtS-LA) with L-Lactide (LA) and Trimethylene Carbonate (TMC)

The polymerization was performed as above but TrtS-LA (0.200 g; 0.50 mmol), LA (0.900 g; 6.25 mmol) and trimethylene carbonate (TMC) (0.535 g; 0.52 mmol) were used as monomers. The polymerization mixture was magnetically stirred for 96 hours. Yield=23%. Composition TrtS-LA:LA:TMC=13:81:6. $M_n$=37.7 kDa ($M_w/M_n$=1.37).

Example 9. Copolymerization of 3-methyl-6-(tritylthiomethyl)-1,4-dioxane-2,5-dione (TrtS-LA) with rac-β-butyrolactone (rac-β-BL)

A previously silanized 25 mL round-bottom flask was charged with a diamine bisphenolate salan yttrium isopropoxide compound (see Scheme 2, 10.0 mg; 15.0 nmol), rac-β-BL (0.11 g; 1.3 mmol), TrtS-LA (0.94 g; 0.23 mmol) and toluene (1.0 mL). The polymerization mixture was thermostated at 70° C. and magnetically stirred for 24 hours. Then, the mixture was cooled down to room temperature, the crude copolymer was dissolved in CH$_2$Cl$_2$ and precipitated twice in heptane. The precipitate was filtered, washed sequentially with MeOH and dried in vacuo at 30° C. overnight. Yield=73%. $M_n$=4410 kDa ($M_w/M_n$=1.1). Composition TrtS-LA:β-BL=20:80.

Scheme 2. Copolymerization of TrtS-LA with β-BL by SalanY(O$^i$PR).

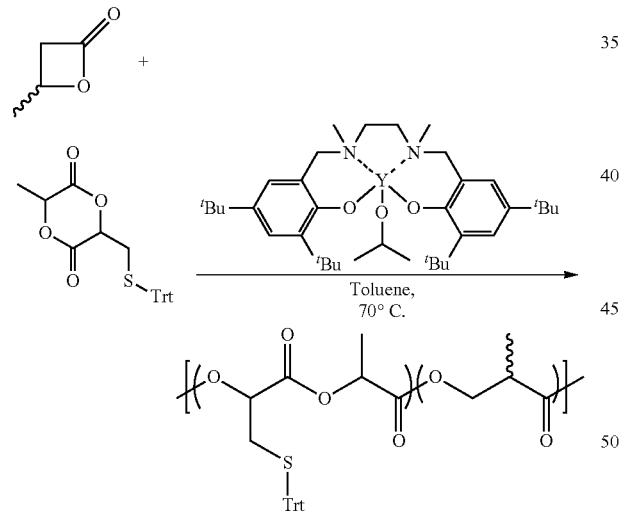

Example 10. Cleavage of Trityl Groups of Poly[(TrtS-LA)-co-CL]

To a solution of poly[(TrtS-LA)-co-CL] (835 mg; 1.15 mmol of TrtS—groups) and Et$_3$SiH (220 μL; 1.38 mmol) in CH$_2$Cl$_2$ (10 mL) was added trifluoroacetic acid (TFA; 600 μL; 8.0 mmol) dropwise over 10 min under nitrogen. The solution was kept under stirring for 1 hour. Then the volatiles were evaporated in vacuo. The crude product (d) was washed with n-hexane and used in the next step without further purification.

Scheme 3. Cleavage of triyl protecting group.

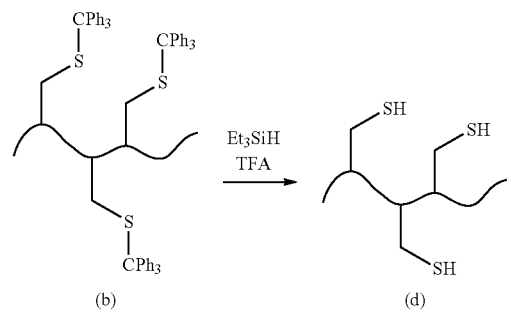

Example 11. Reaction of Poly[(HS-LA)-co-CL] with 2,2'-dipyridyl disulfide

The poly[(HS-LA)-co-CL] obtained in Example 3 was dissolved in CH$_2$Cl$_2$ (45 mL). The solution was added dropwise over 1 hour to a solution of 2,2'-dipyridyl disulfide (PDS, 1.00 g; 4.6 mmol) in CH$_2$Cl$_2$ (5 mL) under nitrogen. The mixture turned yellow and was allowed to stir for three hours. Then, it was concentrated to ~10 mL and poured in 200 mL hexane. The precipitate polymer was washed three times with MeOH, then dried under nitrogen flow and later in vacuo until constant weight. The obtained poly[(PDS-LA)-co-CL] (e) was collected as a clear waxy solid.

Scheme 4. Modification of poly[(HS-LA)-co-CL] to obtain a polymer with pyridyl disulfide pendant groups.

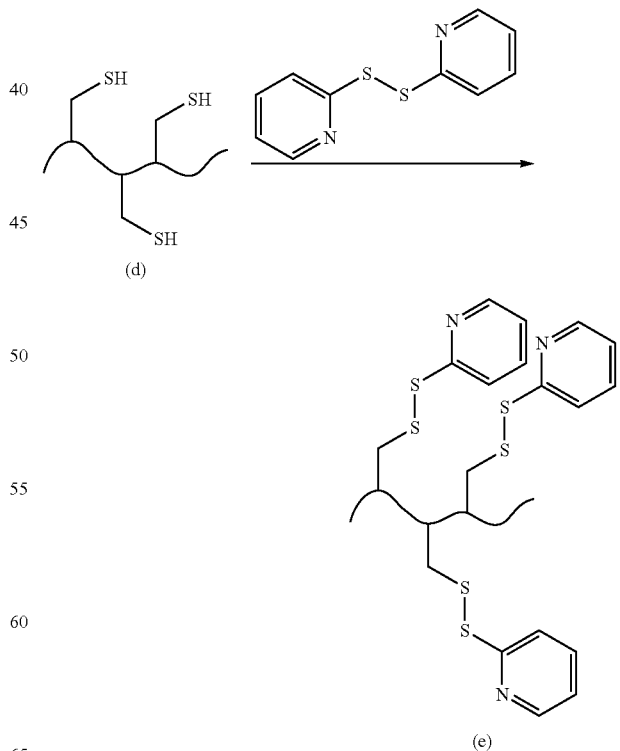

Example 13. Binding of H-Arg-Gly-Asp-Cys-OH (RGDC) Peptide to the Scaffolds

The binding of the RGDC (H-Arg-Gly-Asp-Cys-OH) to the scaffolds was performed according to a slightly modified literature procedure.[30] Porous scaffolds of the polymer from Example 7 (1 mm in thickness and 10 mm in diameter; weight in the range 15.1-11.4 mg; content of pyridyl disulfide groups in the range $2.9$-$6.6 \times 10^{-6}$ mol) were presoaked in ethanol and then in phosphate buffered saline (PBS). Afterwards, scaffolds were transferred to a 2.5 ml of peptide solution ($C = 5.00 \times 10^{-3}$ M) in PBS (C=0.01 M; pH=7.4) and shaken in the dark, at room temperature. UV spectroscopy of the peptide solution was used to follow the reaction; the absorbance of the released 2-pyridinethiol at 343 nm was detected to calculate the degree of immobilization according to Beer's law being known the molar extinction coefficient, $\varepsilon = 8.06 \times 10^3$ M$^{-1}$ cm$^{-1}$, at 343 nm.

Example 14. PEG Conjugation

To a 10 mL glass vial was added poly[(PDS-LA)-co-LLA], having 13 or 17 mol % of PDS-LA units (prepared according to the method described in Example 11 and 12), and 1.1 molar equivalent of PEG-SH (Mn=200 or 800 g mol$^{-1}$). Reagents were dissolved in 7 mL tetrahydrofuran (THF). The reaction was stirred for 18 hours. Films were cast from the PEG-functionalized polymers. To a 10 mL glass vial, 100 mg of polymer was added and dissolved in 1.3 mL of chloroform. The vials were placed on a flat surface, covered with a glass plate, and left to dry for 3 days. After drying the films were immersed in methanol and carefully removed from the vials using tweezers.

Nanoparticles

Poly[(PDS-LA)-co-LA), having from 5, 20 or 30 mol % of PDS-LA units was dissolved in DMF, to this solution a solution of 0.5 molar equivalent HS-PEG-SH ($M_n$, =1000 g mol$^{-1}$) was added. The total polymer concentration was in the range 0.5 to 40.0 mg mL$^{-1}$. The reaction was stirred at room temperature for 24 hours. A solution of nanoparticles in DMF was then dialyzed against deionized water for 24 hours. The size of the nanoparticles determined by DLS was in the range 150-3000 nm.

REFERENCES

1. Seyednejad, H.; Ghassemi, A. H.; van Nostrum, C. F.; Vermonden, T.; Hennink, W. E. *J. Control. Release* 2011, 152, 168-176.
2. Solladie, G.; Boeffel, D.; Maignan, J.; 1996, U.S. Pat. No. 5,523,319
3. Arhancet G. B.; Mahoney, M.; Wang, X. 2013, US20130209392 A1
4. Stenzel, M. H. *ACS Macro Lett.* 2013, 2, 14-18.
5. (a) Trollsås, M.; Hawker, C. J.; Hedrick, J. L.; Carrot, G.; Hilborn, J. *Macromolecules* 1998, 31, 5960-5963. (b) Carrot G, G; Hilborn, J.; Trollsås, M.; Hedrick, J. L. *Macromolecules* 1999, 32, 5264-5269. (c) Hedfors, C.; Östmark, E.; Malmström, E.; Hult, K.; Martinelle, M. *Macromolecules* 2005, 38, 647-649. (d) Kryuchkov, M. A.; Qi, Y. H.; Perepichka, I. I.; Pelletier, C.; Regnaud, A.; Song, Z.; Varshney, S. K. *React. Funct. Polym.* 2015, 90, 1-6.
6. (a) Sourkohi, B. K.; Cunningham, A.; Zhang, Q.; Oh, J. K. *Biomacromolecules* 2011, 12, 3819□3825. (b) Ko, N. R.; Oh, J. K. *Biomacromolecules* 2014, 15, 3180-3189.
7. (a) Kato, M.; Toshima, K.; Matsumura, S. *Biomacromolecules* 2009, 10, 366-373. (b) Tanaka, A.; Masuri, K.; Takighchi, T.; Kato, M.; Matsumura, S. *Polym. Degrad. Stab.* 2012, 97, 1415-1422.
8. Yamamoto, K.; Takasu, A. *Macromolecules* 2010, 43, 366-373.
9. Pappalardo, D.; MaTherg, S.; Finne-Wistrand, A.; Albertsson, A.-C. *J. Polym. Sci., Part A: Polym. Chem.* 2012, 50, 792-800.
10. Goethals, F.; Frand, D.; Du Prez, F. Protected thiol strategies in macromolecular design. *Prog Polym Sci* 2016, http://dx.doi.org/10.1016/j.propolymsci.2016.09.003
11. Fuoco T.; Finne-Wistrand A.; Pappalardo, D., *Biomacromolecules*, 2016, 17, 1383-1394
12. Pappalardo, D.; Tedesco, C.; Pellecchia C., 2002, *Eur. J. Inorg. Chem.*, 621-628

The invention claimed is:

1. A monomer having a structure according to formula (1):

wherein $R_1$ is selected from a group consisting of:

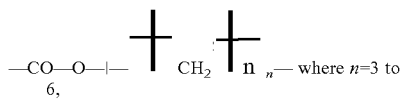

where n=3 to 6,

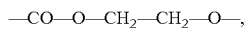

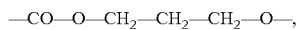

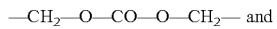 and

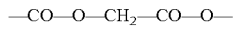

and $R_2$ is any suitable leaving group that may be cleaved and give rise to the formation of a SH group or a S—S bond with proviso that said cleaving and formation does not degrade the ester bonds of the polyester chain; and wherein $R_2$ is selected from the group consisting of p-methoxybenzyl, trityl, monomethoxytrityl, trimethoxybenzyl, 9-xanthenyl 2,2,4,6,7-pentamethyl-5-dihydrobenzofuranylmethyl, tert-butyl, 1-adamantyl, 2-(2,4-dinitrophenyl)ethyl, acetamidomethyl, phenylacetamidomethyl, tert-butylmercapto, 3-nitro-2pyridinesufenyl, 2-pyridinesulfenyl, allyloxycarbonyl, phenylacetamidomethyl, 5-tert-butylmercapto, 3-nitro-2-pyridinesulfenyl, 2-pyridinesulfenyl, allyloxycarbonyl, nallyoxycarbonyl-N-[2,3,5,6-tetrafluoro-4-8phenylthio)phenyl]aminomethyl o-nitrobenzyl and 4-picolyl.

2. The monomer according to claim 1 wherein $R_1$ is —CO—O—CH(CH$_3$)—CO—O—.

3. The monomer according to claim 1, wherein the $R_2$ group is a trityl group.

4. An oligomer or polymer, having a structure according to formula (2):

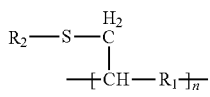

(2)

where n is an integer of 3 or higher, wherein $R_1$ and $R_2$ are as defined in claim 1.

5. The polymer according to claim 4 wherein n is 10 or higher.

6. A copolymer containing from 1 to 95 mol % of a first monomer according to claim 1 and wherein the copolymer further contains at least one second monomer selected from a group consisting of: glycolide, lactide, trimethylene carbonate, caprolactone, paradioxanone, β-butyrolactone and 1,5-dioxepan-2-one.

7. The copolymer according to claim 6 wherein the second monomer is lactide selected from the group consisting of: d,d-lactide, 1, l-lactide, meso lactide, and a racemic mixture of lactides.

8. The copolymer according to claim 6 wherein the second monomer is caprolactone.

9. The copolymer according to claim 6 wherein the copolymer comprises at least to second monomers and wherein said at least two second monomers are selected from lactide, trimethylene carbonate, glycolide and caprolactone.

10. The copolymer according to claim 6, wherein the number average molecular weight ($M_n$) of the copolymer is at least 1,000 g/mol.

11. The copolymer according to claim 6, wherein the copolymer is a segmented copolymer or a random copolymer.

12. The copolymer according to claim 6 wherein $R_1$ in the first monomer is —CO—O—CH(CH$_3$)—CO—O—.

13. The copolymer according to claim 6, wherein $R_2$ in the first monomer is a trityl group.

14. A copolymer composition comprising a copolymer according to claim 6 and a polymer comprising at least one monomer selected from the group consisting of glycolide, lactide, trimethylene carbonate, caprolactone, paradioxanone, β-butyrolactone and 1,5-dioxepan-2-one.

15. A medical device comprising a polymer according to claim 4.

16. The medical device according to claim 15 wherein the device is a porous scaffold.

17. A medical implant comprising a polymer according to claim 4.

18. A film comprising a polymer according to claim 4.

* * * * *